(12) United States Patent
Crivello et al.

(10) Patent No.: US 6,414,168 B1
(45) Date of Patent: *Jul. 2, 2002

(54) EPOXIDATION OF RICINIC COMPOUNDS USING A PHASE-TRANSFER CATALYST

(75) Inventors: James V. Crivello, Clifton Park; Srinivasan Chakrapani, Huntington, both of NY (US)

(73) Assignee: CasChem, Inc., Bayonne, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/473,116

(22) Filed: Dec. 28, 1999

Related U.S. Application Data

(63) Continuation-in-part of application No. 09/220,605, filed on Dec. 28, 1998, now Pat. No. 6,051,725.

(51) Int. Cl.[7] ............................................. C07D 301/12
(52) U.S. Cl. ........................ 549/524; 549/531; 549/561; 549/562
(58) Field of Search ................................ 549/524, 531, 549/561, 562

(56) References Cited

U.S. PATENT DOCUMENTS

| | | | |
|---|---|---|---|
| 2,786,854 A | 3/1957 | Smith et al. | 260/348.5 |
| 2,833,787 A | 5/1958 | Carlson et al. | 260/348.5 |
| 3,351,635 A | 11/1967 | Kollar | 260/348.5 |
| 3,778,451 A | 12/1973 | Poite | 260/348.5 L |
| 3,806,467 A | 4/1974 | Watanabe et al. | 252/429 R |
| 3,953,480 A | 4/1976 | Delavarenne et al. | 260/348.5 L |
| 4,026,908 A | 5/1977 | Pralus et al. | 260/348.5 L |
| 4,197,161 A | 4/1980 | Friedrich et al. | 201/31 |
| 4,303,586 A | 12/1981 | Schirmann et al. | 260/348.31 |
| 4,845,252 A | 7/1989 | Schmidt et al. | 549/531 |
| 4,973,718 A | 11/1990 | Buchler et al. | 549/531 |
| 5,274,140 A | 12/1993 | Venturello et al. | 549/531 |
| 5,336,793 A | 8/1994 | Gardano et al. | 554/138 |
| 5,430,161 A | 7/1995 | Brown et al. | 549/531 |

FOREIGN PATENT DOCUMENTS

| | | |
|---|---|---|
| BE | 860776 | 5/1978 |
| GB | 837464 | 6/1960 |

OTHER PUBLICATIONS

S. Chakrapani and James v. Crivello, Journal of Macromolecular Science, "Synthesis and Photoinitiated Cationic Polymerization of Epoxidized Castor Oil and Its Derivatives," pp. 1–20 (1998).

Jian et al., "J. Polymer Sci: Part A: Polymer Chemistry," vol. 29, pp. 547–553, 1991.

C. Venturello and R. D'Aloisio, "Quaternary Ammonium Tetrakis(diperoxotungsto)phosphates(3–) as a New Class of Catalysts for Efficient Alkene Epoxidation with Hydrogen Peroxide," 53 J. Org. Chem 7 (1988), pp. 1553–1557.

T. W. Findley, D. Swern, & J. T. Scanlan, 67 J. Am. Chem. Soc. (Mar. 1945), "Epoxidation of Unsaturated Fatty Materials with Peracetic Acid in Glacial Acetic Acid Solution," pp. 412–414.

*Primary Examiner*—Ba K. Trinh
(74) *Attorney, Agent, or Firm*—Pennie & Edmonds LLP

(57) ABSTRACT

Unsaturated or polyunsaturated, conjugated or nonconjugated hydrocarbons are reacted with an oxidizing agent including hydroperoxides and monopersulfate compounds in the presence of phase-transfer catalysts. Suitable hydrocarbons include ricinic compounds such as castor oil and dehydrated castor oil. The phase-transfer catalysts include novel tungsten peroxo complexes, such as quaternary ammonium tetrakis (diperoxotungsto) phosphates, and crown ethers. Other additives utilized include pH buffers and alkaline compounds including alkali metal and alkaline earth metal carbonates, and solvents.

19 Claims, No Drawings

EPOXIDATION OF RICINIC COMPOUNDS USING A PHASE-TRANSFER CATALYST

This is a continuation-in-part of application Ser. No. 09/220,605 filed Dec. 28, 1998, now U.S. Pat. No. 6,051,725.

TECHNICAL FIELD

The present invention relates to the catalytic epoxidation of olefins. In particular, the present invention relates to the formation of epoxides from ricinic compounds utilizing oxidizing agents in the presence of phase-transfer catalysts and alkali metal or alkaline earth metal carbonates.

BACKGROUND OF THE INVENTION

Photopolymerization or "UV curing" offers a rapid, environmentally compatible and economically attractive method for preparing three dimensional polymer networks. Consequently, UV curing has been widely used for thin film applications such as coatings, inks, and adhesives. Due to the development of diaryliodonium and diarylsulfonium salts as two classes of practical cationic photoinitiators, this area of polymer photochemistry has enjoyed rapid development over the past two decades and has been applied to the polymerization of a wide range of monomer types.

One of the challenges in polymer chemistry is to develop such polymeric materials from inexpensive, environmentally compatible and renewable sources of starting materials while using the least energy input possible.

Previously, unsaturated plant oils have been modified to provide inexpensive monomers which will polymerize rapidly under photoinitiated cationic polymerization conditions. For example, numerous epoxidized triglyceride oils have been utilized as starting materials to make cross-linked polymer networks.

Due to the lack of reactive functionalities, plant oils (e.g., glycerol triesters of unsaturated fatty acids) are not directly amenable to cationic polymerization. However, the olefinic double bonds of these oils can be readily transformed into cationically polymerizable epoxy groups through simple epoxidation reactions. Conventional epoxides and methods for epoxidation have employed oxidation over silver with ethylene, peroxy acids such as peracetic acid in acetic acid solution, organic peroxides, permanganates, chromates, or dehydrochlorination of chlorohydrins with caustic alkenes.

Under ordinary epoxidizing conditions, e.g. utilizing peracetic acid, the yield of epoxidized castor oil is very low. In addition, the use of conventional epoxidizing agents can create safety and environmental concerns. For example, acetic acid is discharged as a polluting by-product.

Catalysts are utilized in the reaction to provide the highest percentage of epoxy groups. Suitable catalysts include heavy metal catalysts such as a tungsten containing heteropolyacid supported on a solid (U.S. Pat. No. 5,430,161 to Brown et al.), catalytic compounds of molybdenum, tungsten, titanium, columbium, tantalum, rhenium, selenium, chromium, zirconium, tellurium, and uranium (U.S. Pat. No. 3,351,635 to Kollar), an acid salt of a peracid of a heavy metal of the group consisting of tungsten and molybdenum (U.S. Pat. No. 2,833,787 to Carlson et al.), a peracid catalyst of the group consisting of the peracids of tungsten, vanadium, and molybdenum (U.S. Pat. No. 2,786,854 to Smith et al.), a compound of a transition metal such as tungsten in the form of tungsten salts or metallo-organic compounds (U.S. Pat. No. 4,197,161 to Friedrich et al.), a catalyst which is a metal of groups IVA, VA, or VIA, preferably molybdenum or tungsten (Belgian Patent 860,776), and a catalyst selected from elementary boron, a mineral or organic derivative of boron, or mixtures thereof (U.S. Pat. No. 4,303,586 to Schirmann et al.).

Other reactions utilize combinations of catalysts or combinations of catalysts and other reagents. These catalysts or catalytic systems include at least one inorganic or organic derivative or compound of mercury and at least one inorganic or organic derivative of transition elements such as tungsten (U.S. Pat. No. 4,026,908 to Pralus et al.), at least one lead compound and at least one compound of a transition metal such as tungsten (U.S. Pat. No. 3,953,480 to Delavarenne et al.), at least one organic tin compound and a second compound selected from molybdenum, tungsten, vanadium, selenium, boron, and mixtures thereof (U.S. Pat. No. 3,806,467 to Watanabe et al.), a transition compound of a metal such as tungsten and a nitrogenous organic base (U.S. Pat. No. 3,778,451 to Poite), tungstic acid and alkaline salts thereof and an onium salt acting as a phase-transfer agent (U.S. Pat. No. 5,336,793 to Gardano et al.), and a catalytic concentration of a peracid of an oxide of a metal from Groups IV, V, VI, or VIII or a peracid of a heteropolyacid and an inorganic or organic alkaline-reacting substance (Great Britain Patent 837,464).

Although these reactions work well for some unsaturated hydrocarbons, success is not universal. One notable exception is castor oil. A review of recent literature contains few references to the preparation of epoxidized castor oil, suggesting that it has found few applications as compared to other epoxidized vegetable oils. In addition, tungsten-based catalysts have previously been recognized as suitable for use with only a few olefins (U.S. Pat. No. 4,973,718 to Buchler et al. and U.S. Pat. No. 4,845,252 to Schmidt et al.).

A need exists for a method for the epoxidation of castor oil and its derivatives using catalysts, either alone or in combination with additional reagents, that produces a high yield of epoxidized castor having sufficient oxirane oxygen content. The epoxidation reaction should avoid side reactions that adversely effect the stability of the oxirane rings by employing a high efficiency catalyst thus permitting shorter contact times. Further, the epoxidized compounds so produced should be particularly well suited for use in cationic photopolymerization reactions to produce three dimensional polymer networks.

SUMMARY OF THE INVENTION

The present invention is directed to the synthesis of epoxidized castor oil (ECO) as an interesting and inexpensive biorenewable monomer by a novel, surprisingly efficient and low cost epoxation process.

The method of the present invention is a new catalytic method using phase-transfer catalysts. In one embodiment, a novel tungsten peroxo complex based phase-transfer catalyst having onium moieties of suitable lipophilic character is used. In another embodiment, the phase-transfer catalyst is a crown-ether such as 18-crown-6-ether. The new method provides excellent yields of epoxidized castor oil under mild conditions and using an inexpensive, environmentally attractive process. This process can be employed to industrially synthesize epoxidized castor oil which is useful in UV curable coatings, inks, and adhesives. Typically, the epoxidation is rapid, efficient and gives quantitative yields of the desired epoxidized vegetable oils. The epoxidation reaction is also useful for castor oil derivatives such as dehydrated castor oil. As solvents are not required for the epoxidation reaction, solvent removal following epoxidation would not be necessary.

Epoxides are created by the present process by reacting unsaturated or polyunsaturated, conjugated or nonconjugated hydrocarbons with an oxidizing agent including hydroperoxides and monopersulfate compounds in the presence of catalysts that are novel tungsten peroxo complexes. Other additives may be utilized to maintain the pH of the reaction mixture or to increase the yield of the reaction. These additives include pH buffers, alkaline compounds, solvents, extraction agents, and caustic agents.

The present invention relates to a method for epoxidizing ricinic compounds including combining a ricinic compound and a quaternary ammonium tetrakis(diperoxotungsto) phosphate compound to form a mixture, adding an alkali metal or alkaline earth metal carbonate to the mixture in an amount sufficient to inhibit ring-opening side reactions during epoxidation, adding an oxidizing agent to oxidize the mixture and form an epoxide from the ricinic compound, and recovering the epoxide from the mixture.

In one embodiment, the oxidizing agent includes an aqueous solution of hydrogen peroxide. In another embodiment, the ricinic compound includes castor oil or a ricinic derivative thereof. In yet another embodiment, the quaternary ammonium tetrakis(diperoxotungsto)phosphate compound is methyltri-n-octylammonium diperoxotungstophosphate.

In one embodiment, the mixture is heated to a temperature of about 30° C. to about 90° C. prior to addition of the oxidizing agent, and the oxidizing agent is then added to the heated mixture with stirring for a sufficient time to allow a portion of the compounds to react. In a preferred embodiment, the compounds are continuously stirred for up to 8 hours following the addition of the oxidizing agent, and the reacted mixture is allowed to cool to room temperature before recovering the epoxide. In a more preferred embodiment, the mixture is heated to a temperature of about 60° C. with the oxidizing agent being added over the course of about 4 hours. The resulting mixture is stirred for an additional 4 hours to form the epoxide.

In one embodiment, the alkali metal or alkaline earth metal carbonate is added to the heated mixture prior to the addition of the oxidizing agent. In a preferred embodiment, the oxidizing agent is added with stirring over the course of up to about 6 hours, stirring the reacted mixture for an additional time period of up to about 12 hours, and then cooling the reacted mixture to room temperature before recovering the epoxide. In a more preferred embodiment, the mixture is heated to about 60° C. with the oxidizing agent being added over the course of about 2 hours. The resulting mixture is stirred for about an additional 9 hours.

In one embodiment, the alkali metal or alkaline earth metal carbonate includes calcium carbonate, magnesium carbonate, barium carbonate, sodium carbonate, potassium carbonate, lithium carbonate, or mixtures thereof. In a preferred embodiment, the alkali metal or alkaline earth metal carbonate is calcium carbonate. In one embodiment, the alkali metal or alkaline earth metal carbonate is present in an amount from about 1 to about 10% by weight. In a preferred embodiment, the alkali metal or alkaline earth metal carbonate is present in an amount of about 3% to about 7% and more preferably about 5% by weight.

The present invention is also directed to a method for epoxidizing ricinic compounds including combining a ricinic compound and a quaternary ammonium tetrakis (diperoxotungsto)phosphate compound to form a mixture, adding calcium carbonate to the mixture in an amount from about 1 to about 10% by weight, adding an oxidizing agent to oxidize the mixture and form an epoxide from the ricinic compound, and recovering the epoxide from the mixture.

In one embodiment, the oxidizing agent is an aqueous solution of hydrogen peroxide. In addition, the ricinic compound is castor oil or a ricinic derivative thereof, and the quaternary ammonium tetrakis(diperoxotungsto)phosphate compound is methyltri-n-octylammonium diperoxotungstophosphate. In a preferred embodiment, the mixture is heated to a temperature of about 30° C. to about 90° C. prior to addition of the oxidizing agent. The oxidizing agent is then added to the heated mixture with stirring for a sufficient time to allow a portion of the compounds to react.

In a more preferred embodiment, the calcium carbonate is added to the heated mixture prior to the addition of the oxidizing agent. In another embodiment, the calcium carbonate is present in an amount of about 3% to about 7% and more preferably about 5% by weight.

The present invention is also drawn to a method for epoxidizing ricinic compounds which includes combining dehydrated castor oil and a phase-transfer catalyst to form a mixture; adding an oxidizing agent to the mixture to form an epoxide from the dehydrated castor oil; and recovering the epoxide from the mixture. The preferred phase-transfer catalyst is a crown ether, such as 18-crown-6-ether, and the preferred oxidizing agent is potassium monoperoxysulfate.

In this method, a phosphate buffer can be added to the mixture before the addition of the oxidizing agent to achieve a pH of between about 6.5–8.5, the mixture then being cooled to about 0 to −10° C., and an aqueous solution of sodium hydroxide is added to the mixture following addition of the oxidizing agent to maintain the pH between about 6.5–8.5. In a more preferred embodiment, the pH is about 7.4 and the temperature is about −5° C. If desired, acetone can be combined with the dehydrated castor oil and phase-transfer catalyst before adding the oxidizing agent thereto, or a solvent can be combined with the acetone, dehydrated castor oil, and phase-transfer catalyst before adding the oxidizing agent thereto. Useful solvents for this purpose include chlorinated hydrocarbons.

The present invention also encompasses the epoxides produced by the previously described processes.

DETAILED DESCRIPTION OF THE INVENTION

The present invention can be used to epoxidize the olefinic group

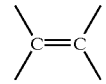

to oxirane

in a wide variety of alkenes. The alkenes may vary according to the type and size of the molecule and the location and number of olefinic groups. The olefinic group or groups may be terminal or embedded in the structure.

Olefinically unsaturated and poly-unsaturated compounds which are epoxidized in accordance with the present invention include substituted and unsubstituted, conjugated and nonconjugated, aliphatic, cycloaliphatic, aromatic, and alicyclic olefins including hydrocarbons, esters, alcohols, ketones, or ethers. Suitable compounds include unsaturated fatty acids including oleic, linoleic, palmitoleic, linoleic, vaccenic, gadoleic, ricinoleic, and eleostearic acids, the natural fats and oils which contain them, and the esters of these unsaturated acids. In a preferred embodiment, the alkene includes castor oil and its ricinic derivatives including ricinoleates, ricinoleic acids, ricinoleic acid amides, ricinoleic acid esters, sulfonated ricinoleates, ricinic alcohols, ricinoleyl acids, ricinoleyl acid amides, ricinoleyl alcohols, ricinoleyl alcohol esters, alkali ricinoleates, ricinolamides, dehydrated castor oil, and mixtures thereof. In a more preferred embodiment, the alkene is castor oil, castor acetate, or dehydrated castor oil. Dehydrated castor oil is commercially available as CASTUNG® oil from CasChem, Inc., Bayonne, N.J.

Castor oil (I) is an inexpensive, biorenewable, large-scale commodity material. Its worldwide production in 1995 alone was 492,254 thousand metric tons.

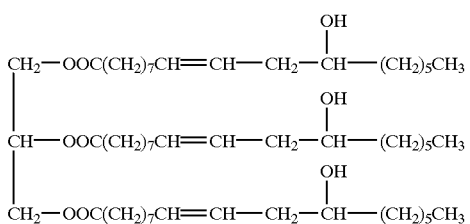

Native and modified castor oils are currently used in many commercial polymer related applications including: plasticizers, nylon intermediates, and polyurethanes. Further, castor oil is an attractive starting material for the synthesis of monomers and polymers because it contains on the average three hydroxyl and three olefinic groups per molecule that can be utilized for introduction of other types of reactive and polymerizable functional groups.

When castor oil is treated with sulfuric or other strong acids it undergoes facile dehydration to give the highly unsaturated oil known as CASTUNG® oil. A generalized structure for CASTUNG® oil (II) is shown in the following reaction.

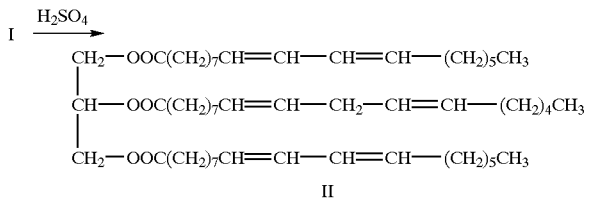

The detailed structure of CASTUNG® oil is far more complicated than the generalized structure shown. Both conjugated and non-conjugated double bonds are present in the oil. The position and number of conjugated double bonds can vary from molecule to molecule and from sample to sample depending on the method of preparation. For example, one type of CASTUNG® oil (II) has a ratio of 28:72 of conjugated to non-conjugated double bonds.

The amount of alkene compound to be epoxidized is selected based upon factors such as the desired quantity of epoxide produced, the required oxirane content of the resultant epoxide and the number of olefinic groups contained within the alkene compound. Preferably, the alkene compound is present in a molar excess over the catalyst.

Olefinic oxidation to produce oxiranes is achieved by the use of oxidizing agents. These oxidizing agents include hydrogen peroxide and monopersulfate compounds. In one embodiment, the monopersulfate is potassium monoperoxosulfate, commercially available as OXONE® compound from E.I. DuPont De Nemours and Company, Wilmington, Del. When the alkene compound is castor oil, the oxidizing compound is preferably hydrogen peroxide. When the alkene compound is CASTUNG® oil, the oxidizing compound is preferably OXONE® compound.

Aqueous hydrogen peroxide ($H_2O_2$) solutions of about 30% to about 90% are acceptable. Preferably, solutions of about 30% and about 70% are used. The amount of hydrogen peroxide added to the reaction can be varied depending upon the strength of the $H_2O_2$ solution, the amount of alkene compound to be epoxidized, or the desired oxirane content of the epoxide. Preferably in the reaction, the molar ratio of the oxidizing agent to the olefin is selected such that there is a slight excess of the oxidizing agent over the number of double bonds in the olefin. Thus, all of the double bonds will be epoxidized, yielding the greatest percentage of oxirane oxygen in the epoxide.

In one embodiment of the method, the oxidizing agent is a 30% aqueous solution of hydrogen peroxide, and the ricinic compound includes castor oil. The quaternary ammonium tetrakis(diperoxotungsto)phosphate includes methyltri-n-octylammonium diperoxotungstophosphate. In this embodiment, the mixture is heated to a temperature of about 30–90° C. and an alkali metal or alkaline earth metal carbonate is added to control pH prior to addition of the oxidizing agent to prevent ring-opening side reactions during formation of an epoxide, adding the oxidizing agent with stirring to the mixture over the course of up to about 8 hours, continuously stirring the mixture for up to an additional 8 hours following addition of the oxidizing agent, and allowing the reacted mixture to cool to room temperature.

In another embodiment, the mixture is heated to about 50°–70° C., adding the alkali metal or alkaline earth metal carbonate followed by addition of the oxidizing agent over the course of up to about 4 hours and stirring the mixture for up to an additional 4 hours. In a more preferred embodiment, the mixture is heated to about 60° C., adding the oxidizing agent over the course of about 4 hours and stirring the mixture for an additional 4 hours.

In another embodiment, the oxidizing agent is a 70% aqueous solution of hydrogen peroxide. In this embodiment, the mixture can be heated to a temperature of about 30–90° C., with addition of the alkali metal or alkaline earth metal carbonate to the mixture prior to the addition of the oxidizing agent. Further, the oxidizing agent can be added with stirring over the course of up to about 6 hours, followed by stirring of the reacted mixture for an additional time period of up to about 12 hours and cooling to room temperature.

In a more preferred embodiment, the mixture is heated to about 50–70° C., and the alkali metal or alkaline earth metal carbonate is added. The oxidizing agent is then added over the course of up to about 2 hours, and the resultant mixture is stirred for an additional time period of up to about 9 hours. In a more preferred embodiment, the mixture is heated to about 60° C., adding the oxidizing agent over the course of about 2 hours and stirring for an additional time period of about 9 hours.

A novel tungsten peroxo complex can be used as a catalyst. This catalyst is generally a quaternary ammonium tetrakis(diperoxotungsto)phosphate(3-). In a preferred embodiment the catalyst is a tetrahexylammonium tetrakis(diperoxotungsto)phosphate(3-) In a more preferred embodiment, the catalyst is methyltri-n-octylammonium diperoxotungstophosphate (MTTP), represented by the formula $[(C_8H_{17})_3N\;CH_3]^+\{PO_4[W(O_2)_2]_4\}^{3-}$.

The epoxidation of castor oil with hydrogen peroxide, both 30% and 70% aqueous hydrogen peroxide have been used, in the presence of MTTP is depicted in the following equation.

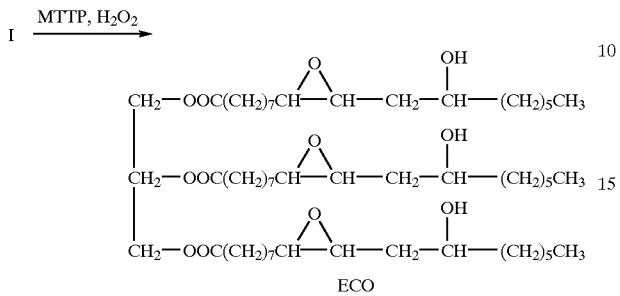

Although other oils and olefins have been used in epoxidation processes, satisfactory results were not previously obtainable using ricinic compounds such as castor oil because of problems arising during the epoxidation process. For example, the level of epoxidation obtained in the final product was lowered due to competing ring-opening side reactions of the epoxide groups under the reaction conditions.

These problems, such as ring-opening side reactions, are avoided through the incorporation of solid, powdered alkali metal or alkaline earth metal carbonate in the reaction mixture. The addition of the alkali metal or alkaline earth metal carbonate helps to control the pH of the reaction mixture. Preferably, the alkali metal or alkaline earth metal carbonate is calcium carbonate, magnesium carbonate, barium carbonate, sodium carbonate, potassium carbonate, lithium carbonate or mixtures thereof. More preferably, the carbonate is an alkaline earth metal carbonate, and most preferably it is calcium carbonate.

The alkali metal or alkali earth metal carbonate is added in an amount sufficient to be present in the reaction in a molar excess to the phase-transfer catalyst. In a preferred embodiment, the amount of alkali metal or alkaline earth metal carbonate is about 1 to about 10% by weight. In a more preferred embodiment, the amount of alkali metal or alkali earth metal carbonate is about 3% to about 7% and most preferably about 5% by weight. ECO with an oxirane oxygen content of 3.6–3.7% can be obtained by the method of the present invention. Based on this determination, it can be calculated that each ECO molecule contains an average of 2.3 epoxy groups.

Epoxidation of CASTUNG® oil with hydrogen peroxide and the MTTP catalyst is possible, but typically results in an epoxidation efficiency of approximately 60%. During the reaction, should the pH of the reaction mixture fall to 4.0, ring-opening of the initially formed epoxy groups can take place as a major and facile side reaction. Incorporation of an alkali metal or alkaline earth metal carbonate into the reaction mixture to control pH is not as effective in increasing the level of epoxidation of CASTUNG® oil as in the epoxidation of castor oil.

The epoxidation of CASTUNG® oil can be achieved using potassium monoperoxysulfate in the presence of the phase-transfer catalyst. Suitable phase-transfer catalysts include the crown ethers. Preferably, the phase-transfer catalyst is 18-crown-6-ether. The addition of acetone helps the reaction proceed smoothly by reacting with the potassium monoperoxysulfate to form an intermediate that epoxidizes. When the pH of the reaction mixture is maintained at 7.4 with the aid of a phosphate buffer, detrimental ring-opening side reactions are avoided. Using potassium monoperoxysulfate as described above, epoxidized CASTUNG® oil (ECT) with an oxirane oxygen content of 6.5% is obtainable. A solvent may also be added to the reaction. Suitable solvents include toluene, hexane and chlorinated hydrocarbons such as dichloromethane. Preferably, the solvent is dichloromethane. Fully epoxidized ECT has a molecular weight of 975.4 g/mol, corresponding to an oxirane oxygen content of 9.8%. Therefore, ECT prepared according to the method of the present invention has approximately four epoxy groups per molecule.

In order to make ECO, castor oil, the phase-transfer catalyst, and the alkali metal or alkaline earth metal carbonate are mixed together. The temperature is raised to about 60° C. Then, the oxidizing agent is added over the course of up to about 2 hours, and the resultant mixture is held at about 60° C. for up to about 9 hours before cooling to room temperature. A solvent such as toluene or chloroform can then be added to extract the product. The organic layer is then separated and dried, and the solvent removed by evaporation.

In order to make ECT, CASTUNG® oil and the phase-transfer catalyst are mixed together. If desired, additional solvents may be added to the mixture at this time. Suitable solvents include acetone and chlorinated hydrocarbons such as dichloromethane. A buffer compound, such as phosphate buffer, is added to the mixture to maintain the pH at about 7.4. The mixture is then cooled to below about 0° C., preferably about −5° C. The oxidizing agent is then added slowly for up to about 4 hours, and a base, such as NaOH in a 2N aqueous solution, is added as well to maintain the pH at about 7.4 during the reaction. The temperature is increased to about 2° C., and the mixture is stirred for up to about an additional 24 hours. The epoxide product is then obtained by filtration, solvent addition, dehydration, and evaporation.

EXAMPLES

ECO and ECT were prepared by the method of the present invention and tested for oxirane content. Castor oil (I) and dehydrated castor oil (CASTUNG® oil, II) were supplied by CasChem, Inc., Bayonne, N.J. OXONE®, 18-crown-6-ether, methyltri-n-octylamine and 30 wt. % hydrogen peroxide were procured from Aldrich Chemical Co., Milwaukee, Wis. Hydrogen peroxide (70 wt. %) was obtained from FMC Corporation, Philadelphia, Pa. MTTP was synthesized according to the procedure reported in literature.

$^1$H NMR spectra were recorded on a Varian XL-200 spectrometer using $CDCl_3$ as the solvent and tetramethylsilane (TMS) as an internal reference. Routine infrared spectra were obtained using a MIDAC Model M1300 FTIR. The percent oxirane oxygen of the epoxidized oils was determined according to ASTM D-1652-88.

Example A

Epoxidation of Castor Oil with 30% Hydrogen Peroxide

To a 5 L three-necked flask equipped with a thermometer, addition funnel, condenser and mechanical stirrer were added castor oil (500 g, 0.54 mol) and methyltri-n-octylammonium diperoxotungstophosphate (MTTP, 3 g, 1.33 mmol). The temperature of the reaction flask was gradually brought to 60° C. and 1070 mL (8.7 mol, 30% aqueous solution) hydrogen peroxide was added with stirring over the course of 4 h using the addition funnel. The reaction mixture was vigorously stirred for an additional 4 h before allowing it to cool to room temperature. Toluene (1 L) was added to extract the product and the organic layer separated and dried over anhydrous sodium sulfate. After the removal of the solvent on a rotary evaporator, epoxidized castor oil (ECO) was recovered in 95% yield. $^{1}$H NMR spectrum of the product revealed that 75% conversion of the double bonds to epoxide groups had taken place. The oxirane oxygen content was determined by ASTM method D-1652-88 and found to be 3.6%.

Example B

Epoxidation of Castor Oil with 70% Hydrogen Peroxide

To a 3 L three-necked flask equipped with a thermometer, condenser and mechanical stirrer were added castor oil (500 g, 0.54 mol) and MTTP 3 g, 1.33 mmol). After thoroughly mixing the MTTP and castor oil at 60° C., powdered calcium carbonate (6.65 g, 50 molar excess over MTTP) was introduced and stirred. Hydrogen peroxide (102 mL of 70% aqueous solution) was added drop-wise with stirring over the course of 2 h with the aid of a syringe pump. The reaction mixture was kept at 60° C. under vigorous stirring conditions for 9 h before allowing it to cool to room temperature. Chloroform (1 L) was added to extract the product and the resulting solution dried over anhydrous sodium sulfate. After the removal of the solvent on a rotary evaporator, there were obtained 495 g (90% yield) of ECO. The oxirane oxygen content by titration was found to be 3.7%.

Example C

Epoxidation of Castung® Oil

To a 3 L three-necked flask equipped with a thermometer, condenser, two addition funnels and a mechanical stirrer was added (11.2 g, 0.013 mol) of Castung® oil and 0.25 g (0.95 mmol) of 18-crown-6-ether along with 50 mL each of acetone and dichloromethane. After the introduction of 200 mL of 7.4 pH phosphate buffer, the contents of the flask were cooled to −5° C. and Oxone® (120 g in 500 mL deionized water) was added drop-wise. During the reaction, a 2N aqueous NaOH solution was added drop-wise along with Oxone® to maintain the pH at approximately 7.4. Complete addition to Oxone® required 4 h and thereafter the reaction mixture was stirred overnight at 2° C. The reaction mixture was filtered, diluted with dichloromethane, dried over anhydrous sodium sulfate and the solvents stripped off using a rotary evaporator. There were recovered 11.9 g (96% yield) of epoxidized Castung® oil (ECT). Titrimetric determination gave an oxirane oxygen content of 6.7%.

Although preferred embodiments of the invention have been described in the foregoing description, it will be understood that the invention is not limited to the specific embodiments disclosed herein, but is capable of numerous modifications by one of ordinary skill in the art. It will be understood that the materials used and the chemical details may be slightly different or modified without departing from the methods and compositions disclosed and taught by the present invention.

What is claimed is:

1. A method for epoxidizing ricinic compounds comprising:

combining a ricinic compound and a quaternary ammonium tetrakis(diperoxotungsto)phosphate compound to form a mixture;

adding an alkali metal or alkaline earth metal carbonate to the mixture in an amount sufficient to inhibit ring-opening side reactions during epoxidation;

adding an oxidizing agent to oxidize the mixture and form an epoxide from the ricinic compound; and, recovering the epoxide from the mixture.

2. The method according to claim 1 wherein the oxidizing agent is an aqueous solution of hydrogen peroxide.

3. The method according to claim 2 wherein the ricinic compound is castor oil or a ricinic derivative thereof.

4. The method according to claim 3 wherein the quaternary ammonium tetrakis(diperoxotungsto)phosphate compound is methyltri-n-octylammonium diperoxotungstophosphate.

5. The method according to claim 4 which further comprises heating the mixture to a temperature of about 30–90° C. prior to addition of the oxidizing agent, and then adding the oxidizing agent to the heated mixture with stirring for a sufficient time to allow the compounds to react.

6. The method according to claim 5 wherein the compounds are continuously stirred for up to 8 hours following the addition of the oxidizing agent, and the reacted mixture is allowed to cool to room temperature before recovering the epoxide.

7. The method according to claim 6 wherein the mixture is heated to a temperature of about 60° C., the oxidizing agent is added over the course of about 4 hours, and the resulting mixture is stirred for an additional 4 hours to form the epoxide.

8. The method according to claim 5, wherein the alkali metal or alkaline earth metal carbonate is added to the heated mixture prior to the addition of the oxidizing agent.

9. The method according to claim 8 further comprising adding the oxidizing agent with stirring over the course of up to about 6 hours, stirring the reacted mixture for an additional time period of up to about 12 hours, and then cooling the reacted mixture to room temperature before recovering the epoxide.

10. The method according to claim 9 wherein the mixture is heated to about 60° C., the oxidizing agent is added over the course of about 2 hours, and the resulting mixture is stirred for about an additional 9 hours.

11. The method according to claim 1, wherein the alkali metal or alkaline earth metal carbonate comprises calcium carbonate, magnesium carbonate, barium carbonate, sodium carbonate, potassium carbonate, or lithium carbonate.

12. The method according to claim 1, wherein the alkali metal or alkaline earth metal carbonate is calcium carbonate.

13. The method according to claim 1, wherein the alkali metal or alkaline earth metal carbonate is present in an amount from about 1 to about 10% by weight.

14. The method according to claim 1, wherein the alkali metal or alkaline earth metal carbonate is present in an amount of about 3% to about 7% by weight.

15. A method for epoxidizing ricinic compounds comprising:

combining a ricinic compound and a quaternary ammonium tetrakis(diperoxotungsto)phosphate compound to form a mixture;

adding calcium carbonate to the mixture in an amount from about 1 to about 10% by weight;

adding an oxidizing agent to oxidize the mixture and form an epoxide from the ricinic compound; and, recovering the epoxide from the mixture.

16. The method of claim 15, wherein:

the oxidizing agent is an aqueous solution of hydrogen peroxide;

the ricinic compound is castor oil or a ricinic derivative thereof; and the quaternary ammonium tetrakis(diperoxotungsto) phosphate compound is methyltri-n-octylammonium diperoxotungstophosphate.

17. The method of claim 16, which further comprises heating the mixture to a temperature of about 30° C. to about 90° C. prior to addition of the oxidizing agent, and then adding the oxidizing agent to the heated mixture with stirring for a sufficient time to allow a portion of the compounds to react.

18. The method of claim 17, wherein the calcium carbonate is added to the heated mixture prior to the addition of the oxidizing agent.

19. The method of claim 15, wherein the calcium carbonate is provided in an amount of about 3% to about 7% by weight.

* * * * *